United States Patent [19]

Sotoya et al.

[11] Patent Number: 5,132,425

[45] Date of Patent: Jul. 21, 1992

[54] QUATERNARY AMMONIUM COMPOUNDS

[75] Inventors: Kohshiro Sotoya; Uichiro Nishimoto; Hiroshi Abe, all of Wakayama, Japan

[73] Assignee: Kao Corporation, Tokyo, Japan

[21] Appl. No.: 646,314

[22] Filed: Jan. 28, 1991

[30] Foreign Application Priority Data

Aug. 13, 1990 [JP] Japan .................. 2-214157

[51] Int. Cl.$^5$ ............... C07D 241/02; C07C 211/00
[52] U.S. Cl. .................... 544/401; 544/358; 544/357; 564/281; 564/290; 564/291; 252/89.1; 252/106; 252/117
[58] Field of Search ............. 544/357, 358, 401; 252/89.1, 106, 117; 564/281, 292, 290

[56] References Cited

U.S. PATENT DOCUMENTS

| | | | |
|---|---|---|---|
| 2,217,846 | 10/1940 | Ortliner et al. | 546/341 |
| 4,139,477 | 2/1979 | Hayek et al. | 564/292 |
| 4,281,196 | 7/1981 | Rutzen et al. | 564/292 |
| 4,304,910 | 12/1981 | Green et al. | 564/292 |
| 4,476,323 | 10/1984 | Hellsten et al. | 564/294 |
| 4,675,180 | 6/1987 | Günter | 564/292 |
| 4,764,306 | 8/1988 | Login | 564/295 |
| 4,778,813 | 10/1988 | Fenyes et al. | 564/292 |
| 4,820,511 | 4/1989 | Hoeffkes et al. | 564/294 |

FOREIGN PATENT DOCUMENTS

| | | | |
|---|---|---|---|
| 252441 | 1/1988 | European Pat. Off. | 564/294 |
| 414574 | 2/1991 | European Pat. Off. | 544/401 |
| 2070040 | 9/1981 | United Kingdom | 564/294 |

Primary Examiner—Cecilia Shen
Attorney, Agent, or Firm—Sughrue, Mion, Zinn, Macpeak & Seas

[57] ABSTRACT

Novel quaternary ammonium compounds of formula (1) and (2):

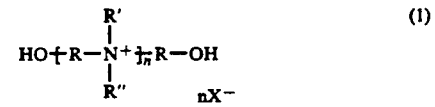

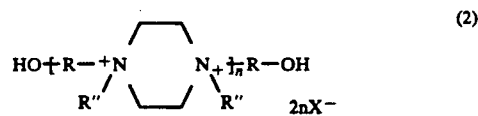

wherein R represents a straight or branched alkylene group containing from 2 to 24 carbon atoms, an alicyclic alkylene group, an aralkylene group or a group of the formula $-(CH_2CH_2O)_p(CH_2CH_2)_q-$ (in which p and q each represents a positive integer), R' represents a straight or branched alkyl group containing from 1 to 24 carbon atoms, an alkenyl group or an aralkyl group, R" represents an alkyl group containing 1 to 5 carbon atoms or an aralkyl group, X$^-$ represents an anionic group and n represents a positive integer of from 2 to 50 are disclosed. The quaternary ammonium compounds are useful as surfactants capable of serving as softening agents and antistatic agents for fabrics, hair and the like.

6 Claims, 2 Drawing Sheets

TERMINAL GROUP QUANTITATION (%) BY $^{13}$C-NMR SPECTROMETRY

...94%

...6%

QUATERNARY AMMONIUM COMPOUNDS

FIELD OF THE INVENTION

This invention relates to novel quaternary ammonium compounds and, more particularly, to novel quaternary ammonium compounds useful a surfactants capable of serving as softening agents and antistatic agents for fabrics, hair and the like.

BACKGROUND OF THE INVENTION

Hitherto, dimethyldioleylammonium chloride and dimethyldi-hydrogenated tallow-ammonium chloride have been used as fabric softeners. However, they cannot meet all the requirements set out from the softening, water-absorbing and antistatic effect or capacity viewpoints.

SUMMARY OF THE INVENTION

Under these circumstances, the present inventors conducted intensive investigations and, as a result, discovered certain novel quaternary ammonium compounds which can meet all the softening, water-absorbing and antistatic property requirements. Based on such finding, they have now completed the present invention.

Thus the invention provides novel quaternary ammonium compounds of formula (1) or (2) given below and surfactant compositions containing such novel quaternary ammonium compounds.

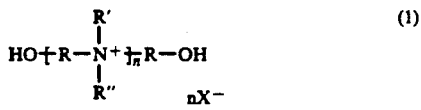

(1)

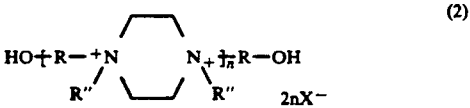

(2)

In formulas (1) and (2), R represents a straight or branched alkylene group containing from 2 to 24 carbon atoms, an alicyclic alkylene group, an aralkylene group or a group of the formula $+CH_2CH_2O)_p$ $+CH_2CH_2)_q$ (in which p and q each represents a positive integer), R' represents a straight or branched alkyl group containing from 1 to 24 carbon atoms, an alkenyl group or an aralkyl group, R" represents an alkyl group containing 1 to 5 carbon atoms or an aralkyl group, X⁻ represents an anionic group and n represents a positive integer of from 2 to 50.

DETAILED DESCRIPTION OF THE INVENTION

Figure 1:
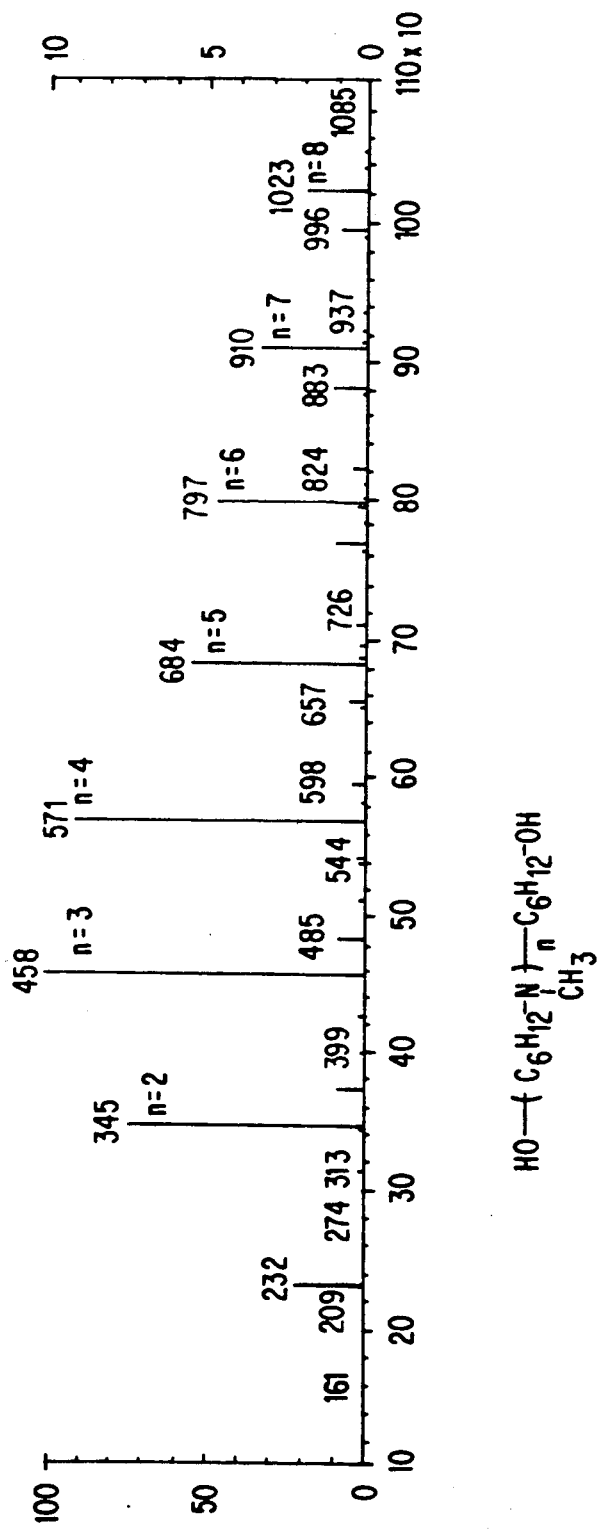
FIG. 1 shows a mass spectrum of the tertiary amino alcohol obtained in Synthesis Example and FIG. 2 shows a $^{13}C$ NMR spectrum thereof.

In the above formulas (1) and (2), the alicyclic alkylene group represented by R contains preferably from 5 to 6 carbon atoms, the aralkylene group represented by R contains preferably from 6 to 10 carbon atoms and the alkenyl group represented by R' contains preferably from 18 to 22 carbon atoms.

The anionic group represented by X is preferably chloride ion, bromide ion and an alkylsulfate ion.

In the above formulas (1) and (2), the aralkyl group represented by R' or R" is preferably a benzyl or phenethyl group. The group represented by R is preferably an alkylene group containing 2 to 20 carbon atoms or a group of the formula $+CH_2CH_2O)_p+CH_2CH_2)_q$ in which $0<p\leq3$ and $1\leq q\leq10$.

The quaternary ammonium compounds represented by formula (1) or (2) can be produced by quaternizing a tertiary amino alcohol of formula (3) or (4) given below with a quaternizing agent.

(3)

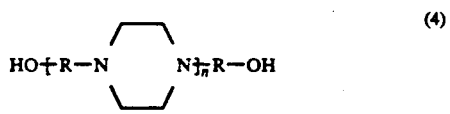

(4)

In formulas (3) and (4), R, R' and n are as defined above.

These tertiary amino alcohols of general formula (3) or (4) are the subject matter of another invention made by the present inventors and disclosed in Japanese Patent Application No. Hei-1-219046 (corresponding to U.S. patent application Ser. No. 07/563,712).

The quaternization of these tertiary amino alcohols can be performed by means of such a quaternizing agent as an alkyl halide (e.g., methyl chloride), an aralkyl halide (e.g., benzyl chloride) or an alkyl sulfate (e.g., dimethyl sulfate, diethyl sulfate). The quaternization may be performed in the presence of water alone or in the presence of an organic solvent such as ethanol or isopropyl alcohol, without any trouble. An appropriate alkali, for example sodium carbonate, may be added for raising the conversion rate. The reaction temperature generally ranges from 30° C. to 100° C.

The quaternary ammonium compounds of the present invention which are represented by the above formula (1) or (2) have surface activity and therefore surfactant compositions containing such compounds as main ingredients can be used as cationic surfactants to serve as basic components of softeners and antistatic agents, among others. Since they have a plurality of cationic groups in their principal chain, the novel quaternary ammonium compounds according to the present invention have a high level of adsorptivity and can produce or impart excellent softening, antistatic and like effects. When R, R' and R" are adequately selected, the quaternary ammonium compounds can be used as basic ingredients in softening formulations without impairing the water-absorbing property of fabrics and in hair rinse and conditioner formulations.

The quaternary ammonium compounds according to the present invention have a hydroxyl group at each end and therefore can be modified in various ways, for example by esterification, to give various derivatives differing in hydrophile/lipophile balance. In other words, they are useful also as intermediates for the synthesis of such derivatives.

The following synthesis and working examples are further illustrative of the present invention. However, they are by no means limitative of the scope of the present invention.

SYNTHESIS EXAMPLE

A tertiary amino alcohol to serve as a raw material was synthesized in the following manner.

A reaction vessel equipped with an inlet tube for hydrogen and gaseous amine and a condenser and a separator for condensing and separating water formed during the reaction, excess amine and oily distillate was charged with 1,200 g of 1,6-hexanediol and 4% by weight, based on the diol, of a copper-based catalyst (Cu-Ni-Pd; mole ratio 4/1/0.1). The contents were stirred and the reaction system atmosphere was replaced with nitrogen, and then the temperature of the reaction system was elevated. After arrival of the system inside temperature at 100° C., hydrogen gas was introduced into the system. After arrival at 180° C., the system inside temperature was maintained at that level and a mixed gas composed of monomethylamine and hydrogen gas was introduced over about 5 hours. After completion of the reaction, the catalyst was filtered off and a pale-brown viscous liquid was obtained.

The pale-brown viscous oil was identified in the following manner.

First, mass spectrometry revealed the presence of tertiary amino alcohols of formula (5) shown below in which n is 1 to 8 as anticipated on the molecular weight basis.

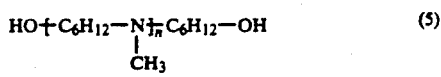

(5)

A mass spectrum for the above product is shown in FIG. 1.

Figure 2:
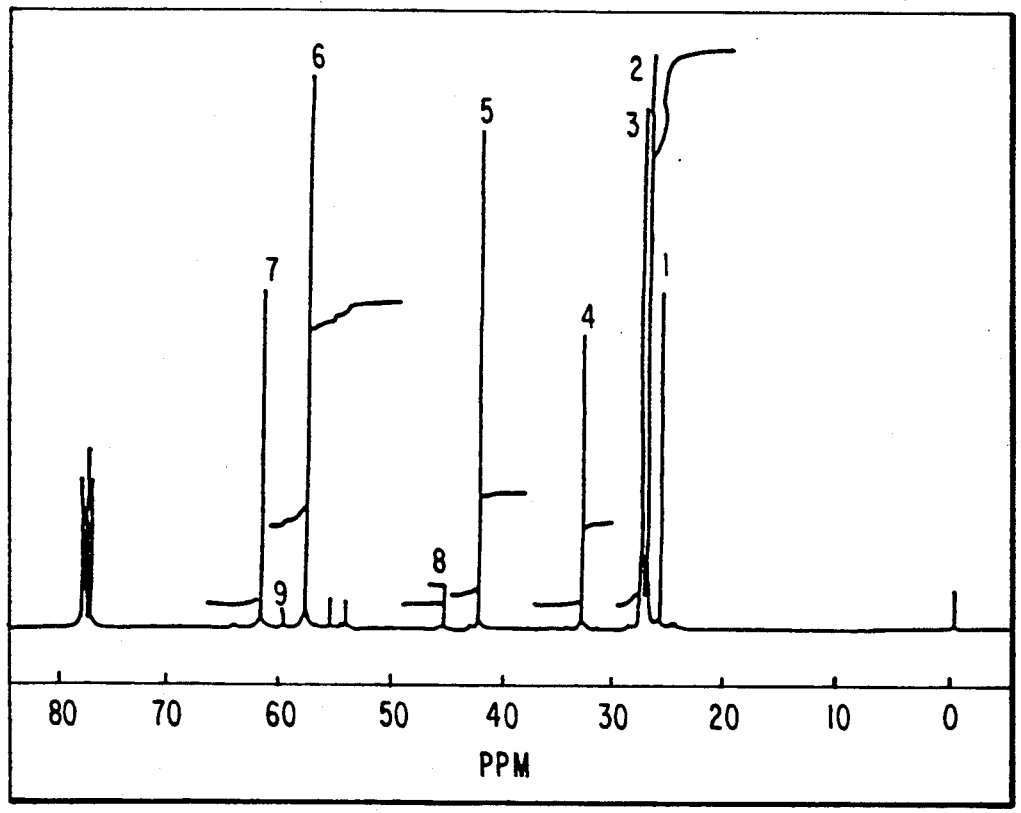
Figure 2:
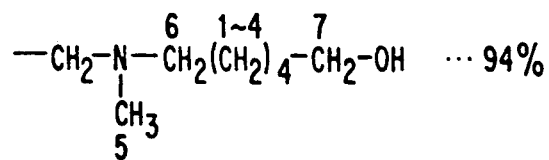
Figure 2:
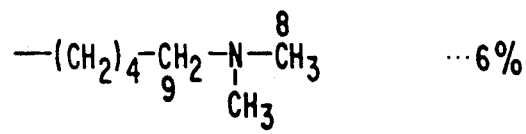

Then, $^{13}$C NMR spectrometry was performed on a 270 MHz NMR spectrometer (JNM-GX270WB) for verifying the terminal alcohol groups. Calculation based on the area ratio data obtained revealed that the alcohol terminus (shown below by formula [1]) accounted for 94% by mole and the dimethylamino terminus (shown below by formula [2]; formed by reaction with dimethylamine formed by disproportionation of monomethylamine) for 6% by mole. The $^{13}$C-NMR spectrum is shown in FIG. 2.

—C$_6$H$_{12}$—OH   (94% by mole)   [1]

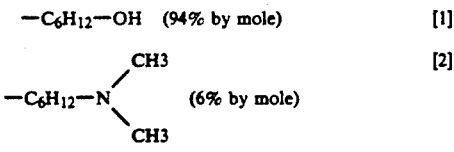

[2]

Furthermore, VPO measurement (vapor pressure osmometric measurement) revealed a molecular weight of 425, and that $\bar{n}$ (the mean value of n) was 2.7. The $\bar{n}$ value calculated from the $^{13}$C-NMR spectrometry data was about 2.4 and was in good agreement with the measured value. The total amine value as measured was 355.7 and the measured tertiary amine value was 353.7, both in good agreement with the theoretical value of 355 calculated for $\bar{n}=2.70$. It was thus confirmed that a mixture of amino alcohols with tertiary amino groups within the principal chain had been produced.

EXAMPLE 1

A one-liter autoclave was charged with 100 g (0.24 mole) of the tertiary amino alcohol obtained in Synthesis Example, 198.5 g of isopropyl alcohol and 12.5 g of sodium carbonate. After further charging of 41.9 g (0.83 mole) of methyl chloride, the autoclave contents were heated to 100° C. with stirring and maintained at that temperature for 5 hours for maturation. The unreacted amine content was determined by titration (residual amine value: 0.87) and the conversion rate was calculated based thereon at 99.3%. The chloride ion was determined to 6.80 and the result was in agreement with the conversion rate of 99.3%. The reaction mixture was cooled to room temperature and then depressurized. The sodium chloride and sodium carbonate were filtered off to give a quaternary ammonium compound (pale yellowish brown liquid) of the formula:

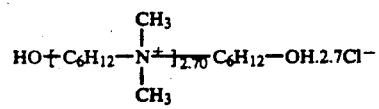

In the above formula, the number 2.70 means the average degree of polymerization.

EXAMPLE 2

A four-necked flask equipped with a stirrer, a condenser, a dropping funnel and a thermometer was charged with 100 g (0.24 mole) of the tertiary amino alcohol obtained in the synthesis example and 723.6 g of water and the charge was heated to 55° C. with stirring. While maintaining that temperature, 85.0 g (0.67 mole) of benzyl chloride was added dropwise to the charge. After completion of the dropping, the reaction mixture was maintained at a temperature of 55°–60° C. for 7 hours for maturation while the pH within the system was maintained at 6.0–8.0 by occasional dropwise addition of 20% aqueous solution of NaOH. The unreacted amine content in the reaction mixture was determined by titration (residual amine value: 1.45) and the conversion rate was calculated based thereon at 96.7%. The chloride ion quantity was 2.43 (corresponding to a conversion rate of 96.8%). The excess benzyl chloride was removed by steam distillation to give a quaternary ammonium compound (pale yellow liquid) of the formula:

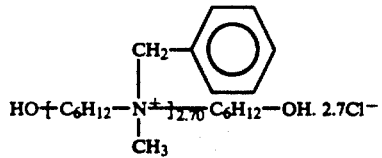

In the above formula, the number 2.70 means the average degree of polymerization.

EXAMPLE 3

A tertiary amino alcohol of formula (3) in which R is —(CH$_2$)$_9$—, R' is —C$_{18}$H$_{37}$, $\bar{M}w$ (the mean molecular weight) is 2090 and $\bar{n}$ is 4.91 was used and the procedure of Example 1 was repeated (residual amine value: 0.41; Cl ion quantity: 3.10; conversion rate: 99.1%, as determined by unreacted amine determination) to give a quaternary ammonium compound (pale yellowish brown liquid) of the formula:

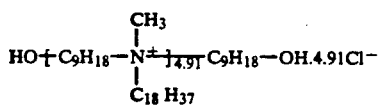

In the above formula, the number 4.91 means the average degree of polymerization.

EXAMPLE 4

A tertiary amino alcohol of formula (3) in which R is —$CH_2)_9$—, R' is —$C_{18}H_{35}$, $\overline{M}w$ is 2040 and $\overline{n}$ is 4.81 was used and the procedure of Example 1 was repeated (residual amine value: 0.54; Cl ion quantity: 2.96; conversion rate: 98.9%, as determined by unreacted amine determination) to give a quaternary ammonium compound (pale yellowish brown liquid) of the formula:

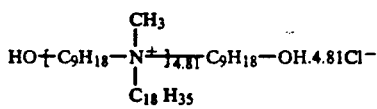

In the above formula, the number 4.81 indicated the average degree of polymerization.

EXAMPLE 5

A tertiary amino alcohol of formula (3) in which R is +$CH_2)_6$—, R' is —$C_{18}H_{35}$, $\overline{M}w$ is 974 and $\overline{n}$ is 2.45 was used and the procedure of Example 1 was repeated (residual amine value: 0.69; Cl ion quantity: 3.13; conversion rate: 98.7%, as determined by unreacted amine determination) to give a quaternary ammonium compound (pale yellowish brown liquid) of the formula:

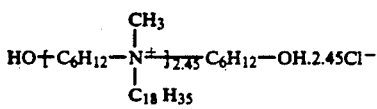

In the above formula, the number 2.45 is the average degree of polymerization.

EXAMPLE 6

A tertiary amino alcohol of formula (3) in which R is +$C_2H_4O)_2$—$(C_2H_4$+, R' is —$C_{18}H_{37}$, $\overline{M}w$ is 1122 and $\overline{n}$ is 2.14 was used and the procedure of Example 1 was repeated (residual mine value: 0.44; Cl ion quantity: 2.44; conversion rate: 98.9%, as determined by unreacted amine determination) to give a quaternary ammonium compound (pale yellowish brown liquid) of the formula:

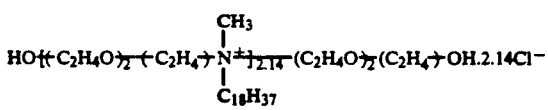

In the above formula, the number 2.14 is the average degree of polymerization.

EXAMPLE 7

A tertiary amino alcohol of formula (4) in which R is +$CH_2)_9$—, $\overline{M}w$ is 650 and $\overline{n}$ is 2.30 was used and the procedure of Example 1 was repeated (residual amine value: 1.96; Cl ion quantity: 7.29; conversion rate: 98.5%, as determined by unreacted amine determination) to give a quaternary ammonium compound (pale yellowish brown liquid) of the formula:

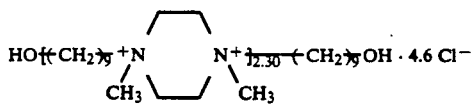

In the above formula, the number 2.30 means the average degree of polymerization.

EXAMPLE 8

The same tertiary amino alcohol as used in Example 3 was quaternized using dimethyl sulfate as the quaternizing agent (residual amine value 12.6). At a conversion rate of 85% (determined by unreacted amine determination), there was obtained a quaternary ammonium compound (pale yellowish brown liquid) of the formula:

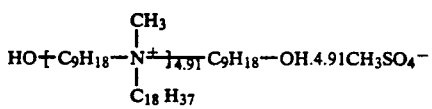

In the above formula, the number 4.91 is the average degree of polymerization.

TEST EXAMPLE

The quaternary ammonium compounds obtained in Examples 1 through 8 were comparatively evaluated from the softening effect, antistatic effect and water absorption viewpoints by the test methods mentioned below.

The results obtained are summarized in Table 1.

Method for treatment:

Marketed cotton knits and acrylic cloths were washed repeatedly five times using the commercial detergent "ATTACK" (trademark, product of Kao Corporation, Tokyo), then rinsed for removing the residual detergent therefrom and treated with an aqueous solution (3.5° DH) containing one of the quaternary ammonium compounds mentioned above as an active ingredient in a concentration of 50 ppm at 25° C. and at a bath ratio (an amount of the cloths/an amount of water) of 1/30 for 5 minutes with agitation.

Methods for evaluation:

Cloths treated in the above manner were dried indoors, then allowed to stand in a constant-temperature, constant-humidity chamber (25° C., 65% RH) for 24 hours, and evaluated for softness, water absorbing capacity and antistatic property.

(1) Softness:

Paired comparison was made using, as a control, a cloth treated with dimethyldioleylammonium chloride (compound for comparison) according to the evaluation criteria given below. The evaluation results were expressed in terms of the mean of scores given by ten panelists.

+2: Softer than the control.
+1: Slightly softer than the control.
0: Substantially equal to the control.
−1: Slightly less soft than the control.
−2: Less soft than the control.

(2) Water absorption:

Test strips (3 cm×20 cm) were cut out from cotton knit underwears respectively treated in the above manner with the quaternary ammonium compounds mentioned above. One end of each strip was immersed in water to a depth of 2 cm and, after 5 minutes, the water front height was measured (in cm).

(3) Antistatic property:

Acrylic cloths were charged at an applied voltage of 7 kV and a target distance of 2 cm using a static honestometer (manufactured by Shishido Shokai). After removal of the voltage, the half-life of the charged voltage was measured (in seconds).

TABLE 1

| Quaternary ammonium compound | Cotton knit | | Acrylic jersey | |
|---|---|---|---|---|
| | Softening | Water absorption (cm) | Softening | Antistatic effect (sec.) |
| Example 1 | +0.5 | 7.5 | +0.7 | 30 |
| Example 2 | +0.5 | 6.5 | +0.5 | 20 |
| Example 3 | +1.5 | 8.2 | +1.5 | 50 |
| Example 4 | +1.5 | 9.0 | +1.5 | 40 |
| Example 5 | +1.5 | 9.5 | +1.5 | 45 |
| Example 6 | +1.5 | 7.6 | +1.5 | 55 |
| Example 7 | +1.0 | 7.5 | +1.0 | 60 |
| Example 8 | +1.5 | 8.5 | +1.5 | 55 |
| Comparative Example 1 | 0 | 8.0 | 0 | 80 |
| Comparative Example 2 | +2.0 | 4.0 | +2.0 | 40 |
| Untreated | −2 | 10.5 | −2.0 | >300 |

Notes:
Comparative Example 1: Treatment with 50 ppm dimethyldioleyl-ammonium chloride;
Comparative Example 2: Treatment with 50 ppm dimethyldi-hydrogenated tallow-ammonium chloride.

From the data shown in Table 1, it is evident that the quaternary ammonium compounds according to the invention can be designed from the molecular structure viewpoint so that they can be excellent in softening and antistatic effects and further from the water absorption viewpoint.

While the invention has been described in detail and with reference to specific examples thereof, it will be apparent to one skilled in the art that various changes and modifications can be made therein without departing from the spirit and scope thereof.

What is claimed is:

1. A quaternary ammonium compound of formula (1) or (2):

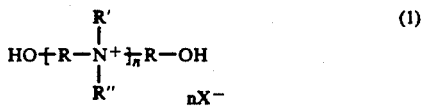
(1)

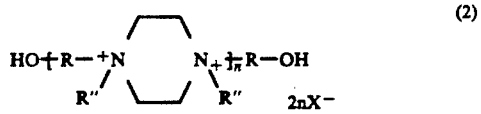
(2)

wherein R represents a straight or branched alkylene group containing from 2 to 24 carbon atoms, an alicyclic alkylene group containing from 5 to 6 carbon atoms, an aralkylene group containing from 6 to 10 carbon atoms or a group of the formula $-(CH_2CH_2O)_p-(CH_2CH_2)_q$ (in which $0 < p \leq 3$ and $1 \leq q \leq 10$), R' represents a straight or branched alkyl group containing from 1 to 24 carbon atoms, an alkenyl group or an aralkyl group selected from benzyl and phenethyl groups, R" represents an alkyl group containing 1 to 5 carbon atoms or an aralkyl group selected from benzyl and phenethyl groups, $X^-$ represents an anionic group and n represents a positive integer of from 2 to 50.

2. A quaternary ammonium compound as claimed in claim 1, wherein R' or R" is a benzyl or phenethyl group.

3. A quaternary ammonium compound as claimed in claim 1 or 2, wherein R is an alkylene group containing 2 to 20 carbon atoms or a group of the formula $-(CH_2CH_2O)_p-(CH_2CH_2)_q$ in which $0 < p \leq 3$ and $1 \leq q \leq 10$.

4. A surfactant composition which comprises a quaternary ammonium compound of claim 1.

5. A surfactant composition which comprises a quaternary ammonium compound of claim 2.

6. A surfactant composition which comprises a quaternary ammonium compound of claim 3.

* * * * *